US010657583B2

(12) United States Patent
Gulfo et al.

(10) Patent No.: US 10,657,583 B2
(45) Date of Patent: May 19, 2020

(54) PHARMACEUTICAL LOCATOR AND INVENTORY ESTIMATION

(71) Applicant: MYLAN, INC., Morgantown, WV (US)

(72) Inventors: Adele Gulfo, New York, NY (US); Rebecca Granne, Sewickley, PA (US); Kristin DiBartolomeo, Morgantown, WV (US); Abigail Kopischke, Rivesville, WV (US); Aaron Harris, Canonsburg, PA (US)

(73) Assignee: Mylan, Inc., Morgantown, WV (US)

( * ) Notice: Subject to any disclaimer, the term of this patent is extended or adjusted under 35 U.S.C. 154(b) by 560 days.

(21) Appl. No.: 14/716,466

(22) Filed: May 19, 2015

(65) Prior Publication Data
US 2016/0342748 A1  Nov. 24, 2016

(51) Int. Cl.
G06Q 30/06 (2012.01)
G06Q 10/08 (2012.01)
G16H 40/20 (2018.01)

(52) U.S. Cl.
CPC ....... G06Q 30/0639 (2013.01); G06Q 10/087 (2013.01); G16H 40/20 (2018.01)

(58) Field of Classification Search
CPC ........ G06Q 50/22; G06Q 10/10; G06Q 50/24; G06Q 10/087; G06Q 40/08; G06Q 10/06; G06Q 20/102; G06Q 30/02; G06Q 30/0283; G06Q 10/08; G06Q 10/109; G06Q 30/0204; G06Q 30/0212; G06Q 30/06; G06F 19/3456; G06F 19/328; G06F 19/3462; G06F 19/327; G06F 19/3406; G06F 19/321; G06F 19/322;
(Continued)

(56) References Cited

U.S. PATENT DOCUMENTS 7,069,226 B1  6/2006  Kleinfelter
7,111,780 B2  9/2006  Broussard et al.
(Continued)

FOREIGN PATENT DOCUMENTS

EP  2256685  12/2010

OTHER PUBLICATIONS

"International Search Report and Written Opinion dated Aug. 22, 2016 for International Application No. PCT/US2016/033072", dated Aug. 22, 2016.
(Continued)

*Primary Examiner* — Rachel L. Porter
(74) *Attorney, Agent, or Firm* — Sorell, Lenna & Schmidt, LLP.; William D. Schmidt, Esq.

(57) ABSTRACT

Various exemplary embodiments relate to a method, device, and storage medium including one or more of the following: receiving, from a user device, a request for pharmaceutical availability, the request including a pharmaceutical identification and a location; identifying a pharmacy near the received location that is known to stock a non-branded pharmaceutical identified by the pharmaceutical identification that is manufactured by a specified pharmaceutical manufacturer; and transmitting the identified pharmacy to the user device, whereby the user device receives a list of at least one nearby pharmacy that carries the non-branded pharmaceutical manufactured by the specified pharmaceutical manufacturer.

19 Claims, 6 Drawing Sheets

(58) Field of Classification Search
CPC .. G06F 19/326; G06F 17/5009; G06F 19/323; G06F 19/3418; G06F 19/3425; G06F 19/3437; G06F 19/345
USPC .......................................................... 705/2, 3
See application file for complete search history.

(56) References Cited

U.S. PATENT DOCUMENTS

| | | |
|---|---|---|
| 7,624,029 B1 | 11/2009 | Ghouri |
| 7,734,483 B1 | 6/2010 | Smith |
| 7,774,134 B1 | 8/2010 | Bleser |
| 7,895,056 B2 | 2/2011 | Liccardo |
| 8,706,522 B2 | 4/2014 | Cohan et al. |
| 8,788,296 B1* | 7/2014 | Ringold .................. G06Q 40/08 705/2 |
| 2004/0138921 A1 | 7/2004 | Broussard et al. |
| 2004/0172281 A1 | 9/2004 | Stanners |
| 2005/0228593 A1* | 10/2005 | Jones ..................... G06Q 10/10 702/19 |
| 2007/0083408 A1* | 4/2007 | Altberg .................. G06Q 30/02 705/14.69 |
| 2012/0101847 A1* | 4/2012 | Johnson .................. G06Q 10/00 705/3 |
| 2012/0253831 A1 | 10/2012 | Pramod et al. |
| 2013/0144649 A1 | 6/2013 | Kalies |
| 2013/0246091 A1 | 9/2013 | Underwood |
| 2013/0275246 A1* | 10/2013 | Ramaratnam ........ G06Q 20/202 705/22 |
| 2013/0304255 A1* | 11/2013 | Ratnakar ................... G07F 9/02 700/242 |
| 2014/0039911 A1 | 2/2014 | Iyer |
| 2016/0125345 A1* | 5/2016 | Majumdar .............. G06F 16/29 705/7.39 |

OTHER PUBLICATIONS

"1mg (Formerly HealthKartPlus)", http://healthkartplus.android.informer.com (Accessed May 19, 2015).

* cited by examiner

| INDIRECT REPORTING TABLE | | | |
|---|---|---|---|
| $x$ = WEEKS SINCE LAST INVOICE | PRESCRIPTION FREQUENCY | | |
| | FAST | MEDIUM | SLOW |
| GREEN | $x <= 2$ | $x <= 12$ | $x <= 26$ |
| YELLOW | $x > 2$ AND $x < 12$ | $x > 12$ AND $x < 26$ | $x > 26$ AND $x < 39$ |
| RED | $x >= 12$ | $x >= 26$ | $x >= 39$ |

| DIRECT REPORTING TABLE | | | |
|---|---|---|---|
| $x$ = WEEKS SINCE LAST INVOICE | PRESCRIPTION FREQUENCY | | |
| | FAST | MEDIUM | SLOW |
| GREEN | $x > 1$ AND $x <= 3$ | $x > 1$ AND $x <= 13$ | $x > 1$ AND $x <= 27$ |
| YELLOW | $x > 3$ AND $x < 13$ | $x > 13$ AND $x < 27$ | $x > 27$ AND $x < 40$ |
| RED | $x <= 1$ OR $x >= 13$ | $x <= 1$ OR $x >= 27$ | $x <= 1$ OR $x >= 40$ |

| DIRECT REPORTING TABLE | |
|---|---|
| $y$ = QUANTITY ON HAND, $z$ = AVERAGE PRESCRIPTION QUANTITY | |
| GREEN | $y >= 3z$ |
| YELLOW | $2z < y < 3z$ |
| RED | $y <= 2z$ |

PHARMACEUTICAL LOCATOR AND INVENTORY ESTIMATION

TECHNICAL FIELD

Various exemplary embodiments disclosed herein relate generally to inventory tracking and, more specifically but not exclusively, to locating pharmacies carrying generic pharmaceuticals using limited information regarding pharmacy inventory.

BACKGROUND

While physicians typically prescribe medications to patients using a trade name, generic versions of the medication are often available at a significantly lower price. When the patient fills a prescription, the pharmacy may offer to provide a generic version, when available at that pharmacy, thus lowering the amount paid by the patient. Generic pharmaceuticals, however, may be manufactured and provided by any of a number of sources. Some patients may hold a higher trust or preference for some generic manufacturers as compared to others. The patient, however, usually isn't provided with a selection between multiple generic sources by the pharmacy; instead, the patient who elects to receive a generic medication will simply be provided with the generic pharmaceutical that the pharmacy happens to have on hand.

SUMMARY

In light of the foregoing, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various exemplary embodiments relate to a non-transitory machine-readable storage medium encoded with instructions for execution by an application server, the non-transitory machine-readable storage medium including: instructions for receiving, from a user device, a request for pharmaceutical availability, the request including a pharmaceutical identification and a location; instructions for identifying a pharmacy near the received location that is known to stock a non-branded pharmaceutical identified by the pharmaceutical identification that is manufactured by a specified pharmaceutical manufacturer; and instructions for transmitting the identified pharmacy to the user device, whereby the user device receives a list of at least one nearby pharmacy that carries the non-branded pharmaceutical manufactured by the specified pharmaceutical manufacturer.

Various exemplary embodiments relate to an application server including: a memory; a network interface; and a processor in communication with the memory and the network interface, wherein the processor is configured to: receive, via the network interface from a user device, a request for pharmaceutical availability, the request including a pharmaceutical identification and a location, identify a pharmacy near the received location that is known to stock a non-branded pharmaceutical identified by the pharmaceutical identification that is manufactured by a specified pharmaceutical manufacturer, and transmit the identified pharmacy to the user device via the network interface, whereby the user device receives a list of at least one nearby pharmacy that carries the non-branded pharmaceutical manufactured by the specified pharmaceutical manufacturer.

Various exemplary embodiments relate to a method performed by an application server, the method including: receiving, from a user device, a request for pharmaceutical availability, the request including a pharmaceutical identification and a location; identifying a pharmacy near the received location that is known to stock a non-branded pharmaceutical identified by the pharmaceutical identification that is manufactured by a specified pharmaceutical manufacturer; and transmitting the identified pharmacy to the user device, whereby the user device receives a list of at least one nearby pharmacy that carries the non-branded pharmaceutical manufactured by the specified pharmaceutical manufacturer.

Various embodiments additionally include determining an availability of the non-branded pharmaceutical at the identified pharmacy, wherein transmitting the identified pharmacy to the user device includes transmitting the identified pharmacy together with the determined availability.

Various embodiments are described wherein determining an availability of the non-branded pharmaceutical at the identified pharmacy includes: determining a frequency of prescription for the identified pharmaceutical; determining, based on transaction data and the prescription frequency, a level of availability for the non-branded pharmaceutical at the identified pharmacy.

Various embodiments are described wherein the transaction data is sales data describing at least one sales transaction providing the non-branded pharmaceutical to a distribution center associated with the pharmacy.

Various embodiments are described wherein the transaction data is chargeback data describing at least one distribution transaction providing the non-branded pharmaceutical to the pharmacy from a distribution center associated with the pharmacy.

Various embodiments are described wherein determining, based on transaction data and the prescription frequency, a level of availability for the non-branded pharmaceutical at the identified pharmacy includes: identifying an applicable rule from a rule table, wherein the applicable rule applies to the transaction data and the prescription frequency and the applicable rule indicates the level of availability.

Various embodiments are described wherein the applicable rule specifies a time interval from a current date, and the transaction data includes a transaction falling within the specified time interval.

BRIEF DESCRIPTION OF THE DRAWINGS

In order to better understand various exemplary embodiments, reference is made to the accompanying drawings, wherein.

DETAILED DESCRIPTION

To provide patients with greater choice in which pharmaceuticals they receive for their prescriptions, various embodiments described herein provide an application that, for an input pharmaceutical name, will provide a list, map, or other indication of nearby pharmacies that stock the generic version of the pharmaceutical from a specific pharmaceutical manufacturer. For example, the application may present only those locations that stock the pharmaceutical as manufactured by Mylan, Inc., so that a patient may choose a pharmacy where the generic provided will be the Mylan generic. In many cases, however, an application provided may not have full visibility of the medications currently on hand at a pharmacy. As such, various embodiments will use available information such as sales and chargeback records to estimate availability of the Mylan generic at each local pharmacy.

Referring now to the drawings, in which like numerals refer to like components or steps, there are disclosed broad aspects of various exemplary embodiments.

Figure 1:
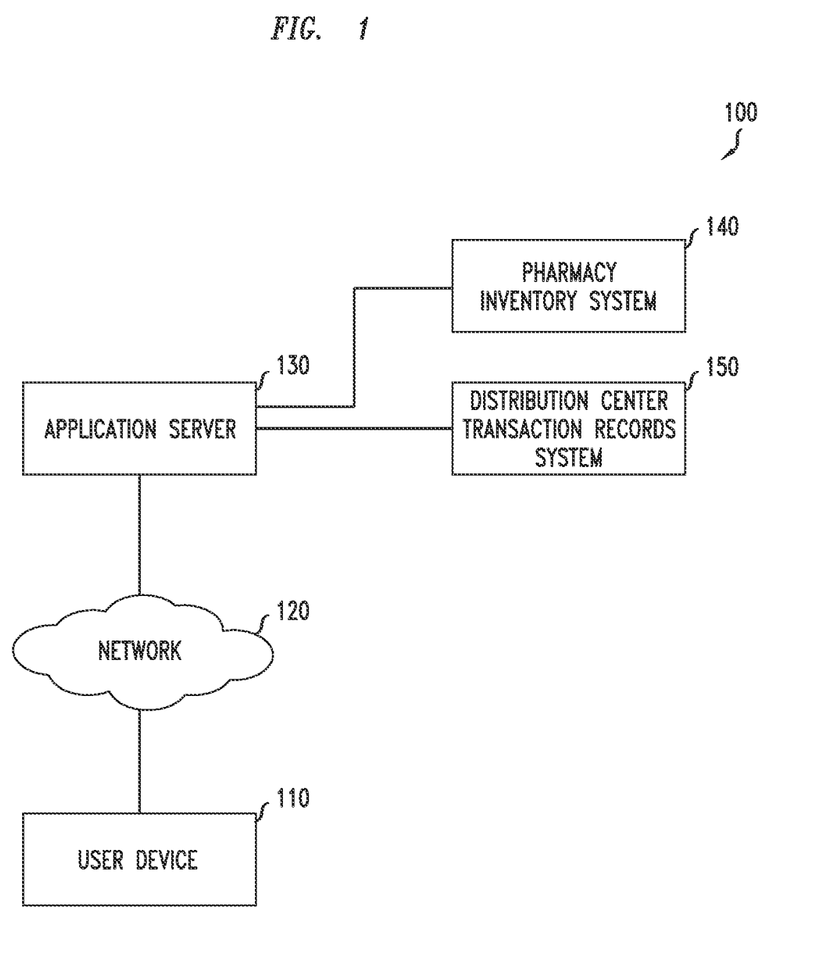
FIG. 1 illustrates an exemplary environment for a generic locator application.

FIG. 1 illustrates an exemplary environment 100 for a generic locator application. As shown, the network includes a user device 110 in communication with an application server 130 over a network 120. The user device 110 may be virtually any device capable of communicating over a computer network 120 such as the Internet including, for example, a mobile phone, a tablet, or a desktop computer. Similarly, the application server 130 may be virtually any device capable of communication over the computer network 120 such as, for example, a server, blade, or desktop computer.

As will be described in greater detail below with respect to various embodiments, the user device 110 executes a client application such as a browser or standalone app that allows a user to select or otherwise input a pharmaceutical name and subsequently requests from the application server a list of local pharmacies stocking a specific generic version of the pharmaceutical. The application server, using available information regarding or otherwise related to pharmacy stock, generates and returns the list of pharmacies, which are then displayed on the user device in a user readable form such as, for example, a map or a list.

The application server 130 bases its decision of whether a particular pharmacy currently stocks the generic from the specific source on a variety of information available to the application server. In various embodiments where the application server 130 is operated by the generic manufacturer, the application server 130 may be provided with sales and inventory data upon which to base this determination. For example, the application server 130 may communicate directly with some pharmacy inventory systems 140. By directly accessing the inventory on hand at a particular pharmacy, the application server 130 may easily make a determination as to whether that pharmacy currently has the generic from the specific source on hand.

While some pharmacies may expose their inventory systems 140 to the application server, not all pharmacies may be so transparent. In fact, in some embodiments, the application server 130 may not have any direct communication with some or all pharmacies. Instead, the application server 130 may be provided with transaction data regarding sales of the generic by the specific source to the pharmacy or a distribution center associated therewith. In such embodiments, the application server 130 may be provided with a list of one or more distribution centers that are known to service each such pharmacy. Then, to estimate the availability of the specific generic at a pharmacy, the application server may retrieve transaction records from a distribution center transaction records system 150 that maintains and provides such information. The distribution center transaction records system 150 may be operated by the distribution center, the pharmaceutical manufacturer, or another entity.

The information available from the distribution center transaction records system 150 may vary between differing distribution centers depending on how each distribution center reports transaction data. Some distribution centers may provide only direct reporting, where sales to the distribution center itself are available but per-pharmacy data is not available. Other distribution centers may alternatively or additionally provide indirect reporting, where chargeback transactions are reported indicating distributions of pharmaceuticals from the distribution center to individual pharmacies. Regardless of the information available, the application server 130 makes an estimation of the availability of the generic at the pharmacy based on the information and reports to the user device 110.

It will be apparent that, while the pharmacy inventory system 140 and distribution center transaction records system 150 are shown as directly attached to the application server 130, either or both of these devices 140, 150 may be in communication with the application server 130 via one or more intermediate device, such as the network 120.

Figure 2:
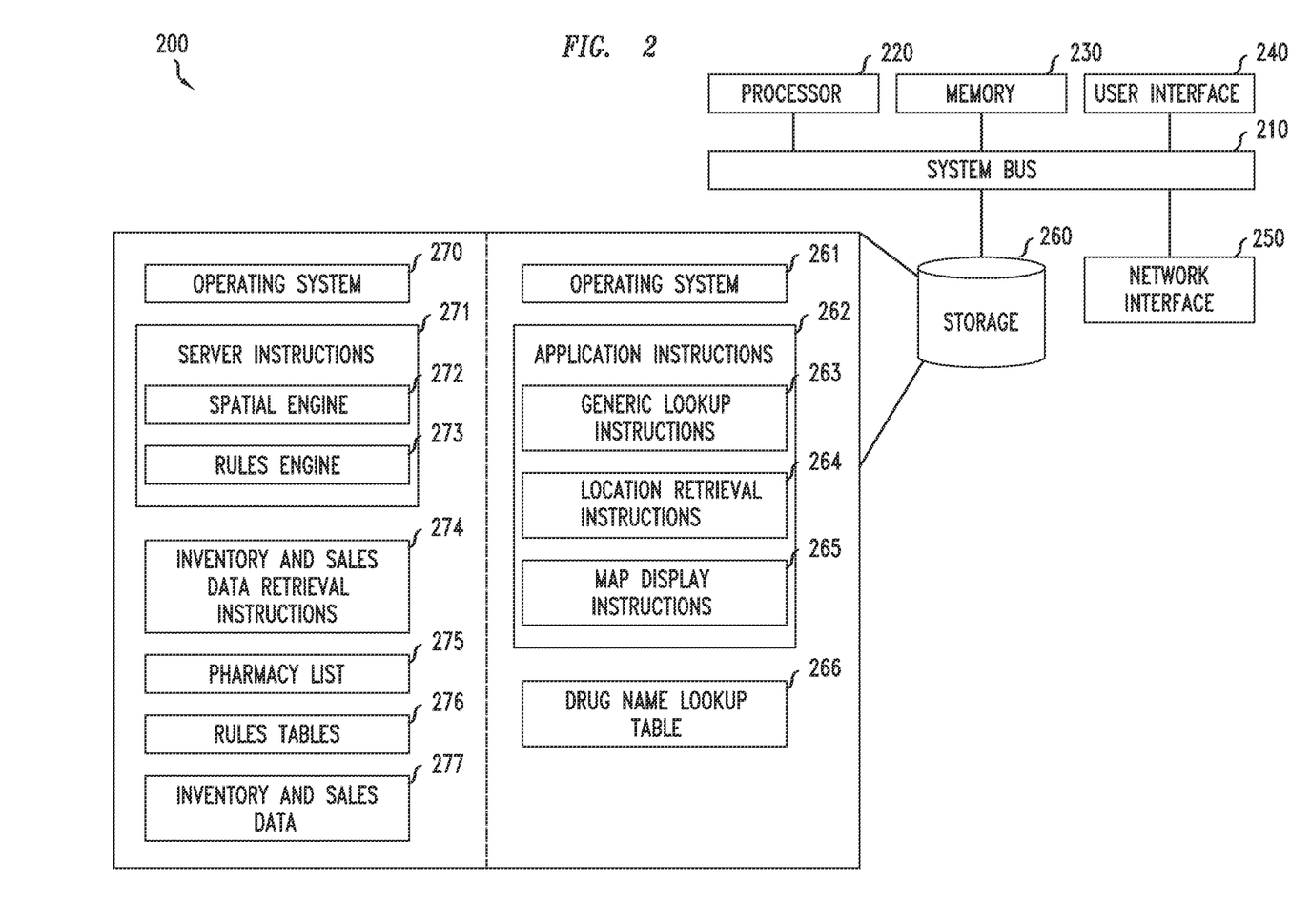
FIG. 2 illustrates exemplary hardware for implementing a user device or an application server.

FIG. 2 illustrates exemplary hardware 200 for implementing a user device or an application server. The exemplary device 200 may correspond to the user device 110 or the application server 130 of FIG. 1. As shown, the device 200 includes a processor 220, memory 230, user interface 240, network interface 250, and storage 260 interconnected via one or more system buses 210. It will be understood that FIG. 2 constitutes, in some respects, an abstraction and that the actual organization of the components of the device 200 may be more complex than illustrated.

The processor 220 may be any hardware device capable of executing instructions stored in the memory 230 or the storage 260. As such, the processor may include a microprocessor, field programmable gate array (FPGA), application-specific integrated circuit (ASIC), or other similar devices.

The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices.

The user interface 240 may include various hardware for enabling interaction with a user of the device 200. For example, the user interface 240 may include a touch screen display, a speaker, and a microphone. In some embodiments, the user interface 240 may include a monitor, a keyboard, and a mouse. Various alternative sets of user input/output hardware will be apparent.

The network interface 250 may include one or more devices for enabling communication with other hardware devices. The network interface 250 may also include one or more wireless interfaces to enable such communications via a wireless communications medium. For example, the wireless interface 250 may include one or more antennae, reception circuitry capable of signal demodulation according to various schemes, transmission circuitry capable of signal modulation according to various schemes, and one or more protocol stacks. The network interface 250 may provide for communication according to one or more wireless protocols such as, for example, WiFi, 3G, 4G, NFC, RFID, or Bluetooth. Such communication may occur directly between the hardware 200 and another device such as a medicament device, or may occur via a network of intermediate devices such as the Internet.

The storage 260 may include one or more machine-readable storage media such as read-only memory (ROM), random-access memory (RAM), magnetic disk storage media, optical storage media, flash-memory devices, or similar storage media.

For example, when the device 200 is a user device, the storage 220 may store operating system instructions 261 for providing various basic functionalities to the system 200 and applications executing on the system. As an example of operating system functionality, the operating system instructions may provide basic input and output functions for outputting various types of alerts such as audible alarms and visual alarms. In some embodiments, the operating system may provide a notification bar or other element for outputting notifications that is always visible while the display of the device 200 is activated and provides icons or other notifications associated with various different applications.

The storage 260 may also include application instructions 262 for controlling the processor to perform various methods similar to those described herein for retrieving and displaying pharmacies and the availability of generic pharmaceuticals from a single specific manufacturer. As part of the application instructions 262, the storage 260 may store generic lookup instructions 263 for looking up a generic drug name corresponding to received input, location retrieval instructions 264 for requesting pharmacy locations from an application server, and map display instructions 265 for displaying received pharmacy locations. Where the application instructions 262 include a web browser application, the generic lookup instructions 263, location retrieval instructions 264, or map display instructions may include instructions downloaded from a web server associated with the application. In various embodiments, drug lookup may be performed locally based on a locally-stored drug name lookup table 266.

Where the device 200 is an application server, the storage 260 may store an operating system 270 and server instructions 271 for processing and responding to requests from application clients. For example, the server instructions 271 may include a spatial engine 272 for identifying pharmacies that are proximate to a requesting device and a rules engine for determining the availability of generic pharmaceuticals from the specific manufacturer at each pharmacy. To support these operations, the storage 260 may also store a list of pharmacies and locations 275, a rules table 276 for determining pharmaceutical availability, and inventory and sales data 277 retrieved from other devices by inventory and sales data retrieval instructions 274.

It will be apparent that various information described as stored in the storage 260 may be additionally or alternatively stored in the memory 230. In this respect, the memory 230 may also be considered to constitute a "storage device." Various other arrangements will be apparent. Further, the memory 230 and storage 260 may both be considered to be "non-transitory machine-readable media." As used herein, the term "non-transitory" will be understood to exclude transitory signals but to include all forms of storage, including both volatile and non-volatile memories.

While the device 200 is shown as including one of each described component, the various components may be duplicated in various embodiments. For example, the processor 220 may include multiple microprocessors that are configured to independently execute the methods described herein or are configured to perform steps or subroutines of the methods described herein such that the multiple processors cooperate to achieve the functionality described herein.

Figure 3:
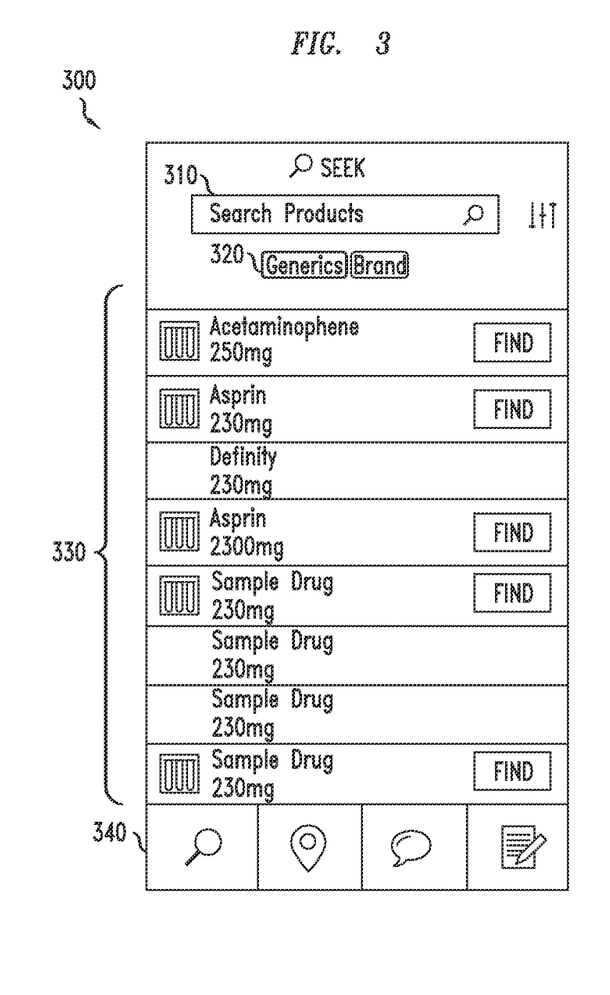
FIG. 3 illustrates an exemplary interface for locating a generic pharmaceutical.

FIG. 3 illustrates an exemplary interface 300 for locating a generic pharmaceutical. This interface 300 may be displayed by a user device for a user to input a pharmaceutical name to be searched among local pharmacies. As shown in the navigation bar 340, the screen may be accessed by the user selecting a "seek" icon.

The interface 300 includes a text input user interface (UI) element 310 for receiving text from a user. Where the interface 300 is displayed on a touchscreen device, upon selection of the text input UI element 310, the user device may display an OS soft keyboard to enable the user to input text. The interface also includes a selector UI element 320 for the user to indicate whether the name being input is a generic or brand name. In other embodiments, the selector UI element 320 may be omitted and the application may search both generic and brand name pharmaceuticals for received input. In some embodiments, the interface 300 may additionally or alternatively include a button to activate a barcode scanner, other optical scanner, near field communication, or other device associated with the device to retrieve information directly from a pharmaceutical or packaging or other information associated therewith. For example, the button may activate a camera of the device which may then be used to capture a barcode displayed on the packaging or container(e.g., where the patient has already filled the prescription once before) or on an advertisement to identify the drug without requiring the user to type in the drug name. In other embodiments, the application may automatically generate a search for a previously-input pharmaceutical based on a determination that the patient is ready to refill the prescription.

After receiving input text via the text input UI element 310, the application searches for pharmaceuticals having the same or a similar name to that which has been input and displays the results in the results list 330. Where the received input text is the same or similar to a brand name pharmaceutical, the results list 330 may include, additionally or instead, corresponding generic drug names. Pharmaceuticals (and dosages thereof) that are available from the specific pharmaceutical manufacturer are provided with a logo or "find" button that may be selected by the user. Upon selection of a drug from the list 330, the user device may transmit a request for a pharmacy list including an identification of the drug (such as the drug name or an identifier) along with a location of the user device to the application server.

Figure 4:
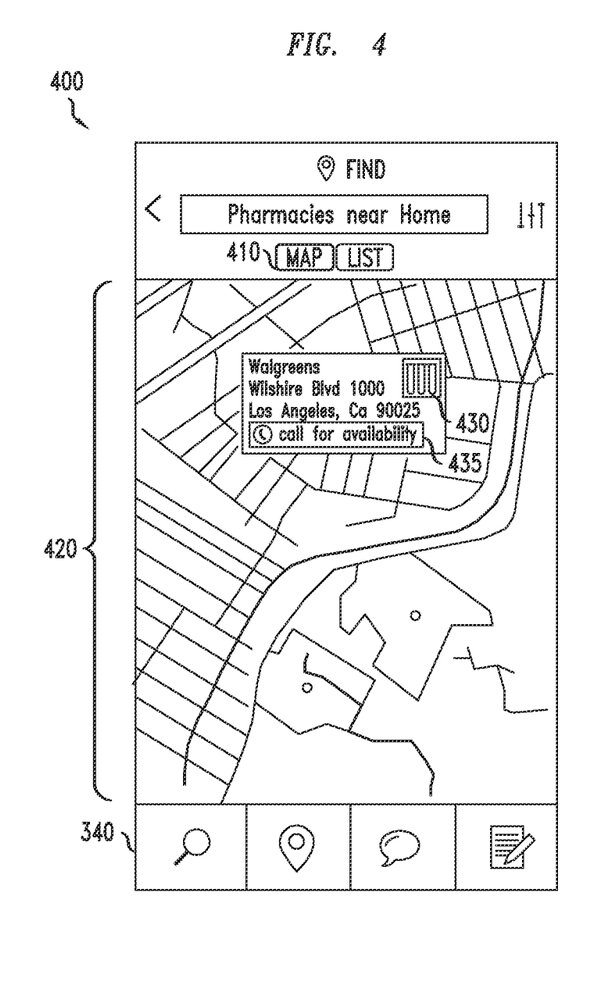
FIG. 4 illustrates an exemplary interface for indicating a location and availability of a generic pharmaceutical.

FIG. 4 illustrates an exemplary interface 400 for indicating a location and availability of a generic pharmaceutical. Upon receiving response to a request for a pharmacy list from the application server, the user device may display an interface similar to the exemplary interface 400. Additionally or alternatively, a recently received pharmacy list may be viewed, as shown in the navigation bar 340, through selection of a "find" icon.

As shown, the interface 400 includes a selector UI element 410 for allowing the user to switch between a map-style view and a list-style view of the received pharmacy list.

The display area 420 currently displays a map-style view indicating a single pharmacy in the viewable area. The pharmacy is identified by a pin icon accompanied by an information window 430 indicating the pharmacy name and location. It will be apparent that alternative or additional information may be included in the information window 430. The information window also includes an availability indication 435. In the specific embodiment shown, the availability indication is a green button with the text "Call For Availability" that, when pressed, will cause the phone OS to initiate a phone call to the specified pharmacy. The green color of the button may indicate that the pharmacy currently has, or is estimated to have, a sufficient stock of the medication to fulfill a prescription. Other colors may be used to indicate other levels of availability. For example, when the application server has determined or estimated the pharmacy to possibly carry sufficient stock to fulfill the prescription (e.g., when the pharmacy has enough of the medication for a two month prescription but not three or more months), the button 435 may be yellow instead. If the pharmacy is determined or estimated to not have enough stock of the medication, the button 435 may instead be red and read "out of stock, call to reorder." It will also be apparent that the availability indicator may take on any form such as a colored or non-colored (non-button) icon, or simple text communicating the availability with varying probability.

The display area 420 may also be used to update the map-type display. For example, through "dragging" and "pinching" gestures, the user may pan or zoom the map respectively. The interface 400 may then be updated to remove or add pharmacies to the map as they come into view. This step may include, in some cases, transmissions of additional requests to the application server for updated lists based on new locations (e.g. when the map is panned) and a new range of distance from the location (e.g., when the map is zoomed).

Figure 5:
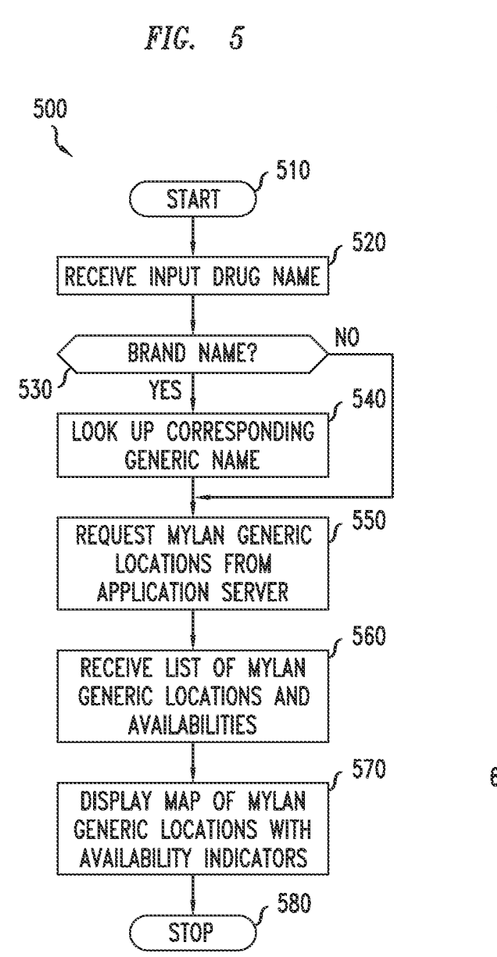
FIG. 5 illustrates an exemplary method for displaying locations and availabilities of a requested generic pharmaceutical.

FIG. 5 illustrates an exemplary method 500 for displaying locations and availabilities of a requested generic pharmaceutical. The method 500 may be performed by the components of a user device such as the user device 110 of FIG. 1 or the components of the hardware device 200 of FIG. 2.

The method begins in step 510 and proceeds to step 520 where the device receives an input drug name from the user. In step 530, the device determines whether the input drug name is a brand name drug by, for example, determining whether a selector UI element such as selector UI element 320 identifies the input as brand name or generic or by referring to a brand name lookup table. If so, the device uses a lookup table or other structure to determine the corresponding generic drug in step 540. At this point, the device may also provide a list of multiple results for further user clarification of intended drug or dosage via user selection from a list (not shown).

After the intended generic drug is determined, the device transmits a request to the application server for a list of pharmacies stocking the generic drug as manufactured by a specific entity (e.g., only those pharmacies that stock the Mylan generic version of the selected drug). This request may include the location of the device and an indication of the identified drug. In response, the device receives a list of pharmacies that are determined to stock the generic along with current determined or estimated availabilities. The device then displays a map of the received locations in step 570 and the method 500 proceeds to end in step 580. It will be apparent that the device may go on to enable additional functionality such as map scrolling and zooming, list updating based on changed view within the map, and facilitating telephone calls to desired displayed pharmacies.

Figure 6:
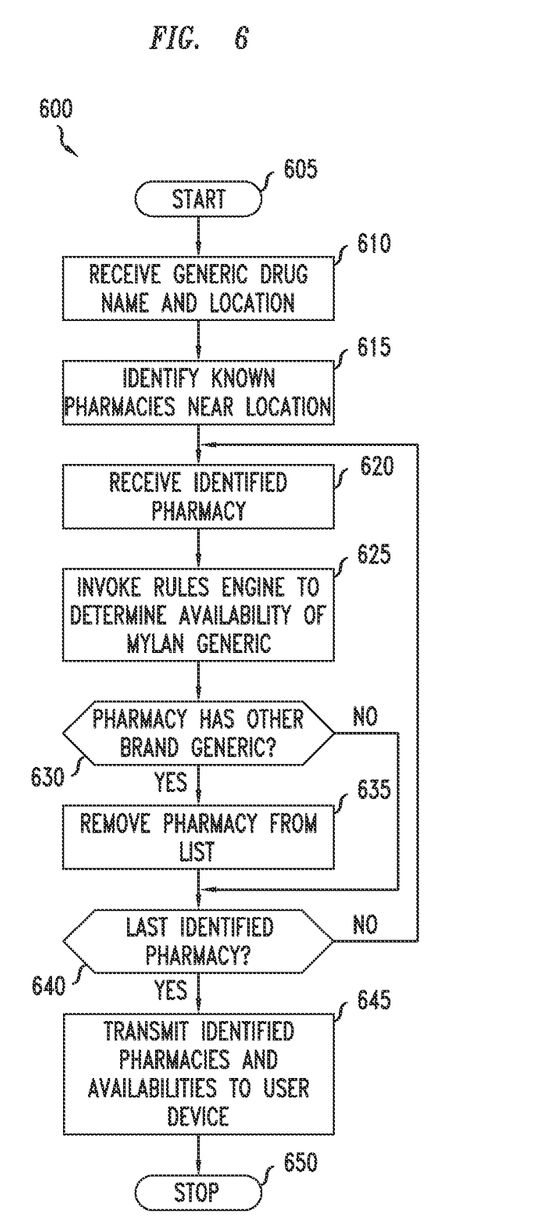
FIG. 6 illustrates an exemplary method of responding to a query for generic pharmaceutical locations and availabilities.

FIG. 6 illustrates an exemplary method 600 of responding to a query for generic pharmaceutical locations and availabilities. The method may be performed by the components of an application server such as, for example the application server 130 of FIG. 1 or the components of the hardware device 200 of FIG. 2.

The method begins in step 605 and proceeds to step 610 where the application server receives a request for a pharmacy list including a generic drug name and location of the requestor. In some embodiments, the request may instead include a brand drug name; in such an embodiment, the application server may translate the brand name to the corresponding generic drug before continuing (not shown). Next, in step 615, the application server identifies the pharmacies known to be near the location carried by the request. For example, the application server may retrieve a list of all pharmacies within 10, 25, or 50 miles of the stated location. In some embodiments, this threshold may be dynamically defined by the user device (through the request) or by the application server (e.g., by gradually increasing the distance until a specified number of pharmacies are located). Various alternative or additional techniques for locating pharmacies proximate a location will be apparent.

Once a list of pharmacies is determined, the application server retrieves a pharmacy to analyze for generic availability. In step 625, the application server invokes a rules engine (an exemplary operation of which will be described below) to determine an availability of the specific generic at the pharmacy. In step 630, the application server determines whether the pharmacy is carrying a generic brand from a manufacturer other than the specific manufacturer to which the application as a whole applies. For example, the application server may determine whether, from the rules engine or from other available data regarding pharmacy stock, that the pharmacy currently stocks the generic drug as manufactured by a company other than Mylan. If so, the application server removes the pharmacy from the list in step 635, so as to not report the location to the user device.

In step 640, the application server determines whether the current pharmacy represents the last pharmacy in the list determined in step 615. If not, and additional pharmacies remain, the method loops back to step 620. Otherwise, in step 645, the application server transmits the list of pharmacies along with determined generic availabilities to the user device in step 645 and the method 600 proceeds to end in step 650.

Figure 7:
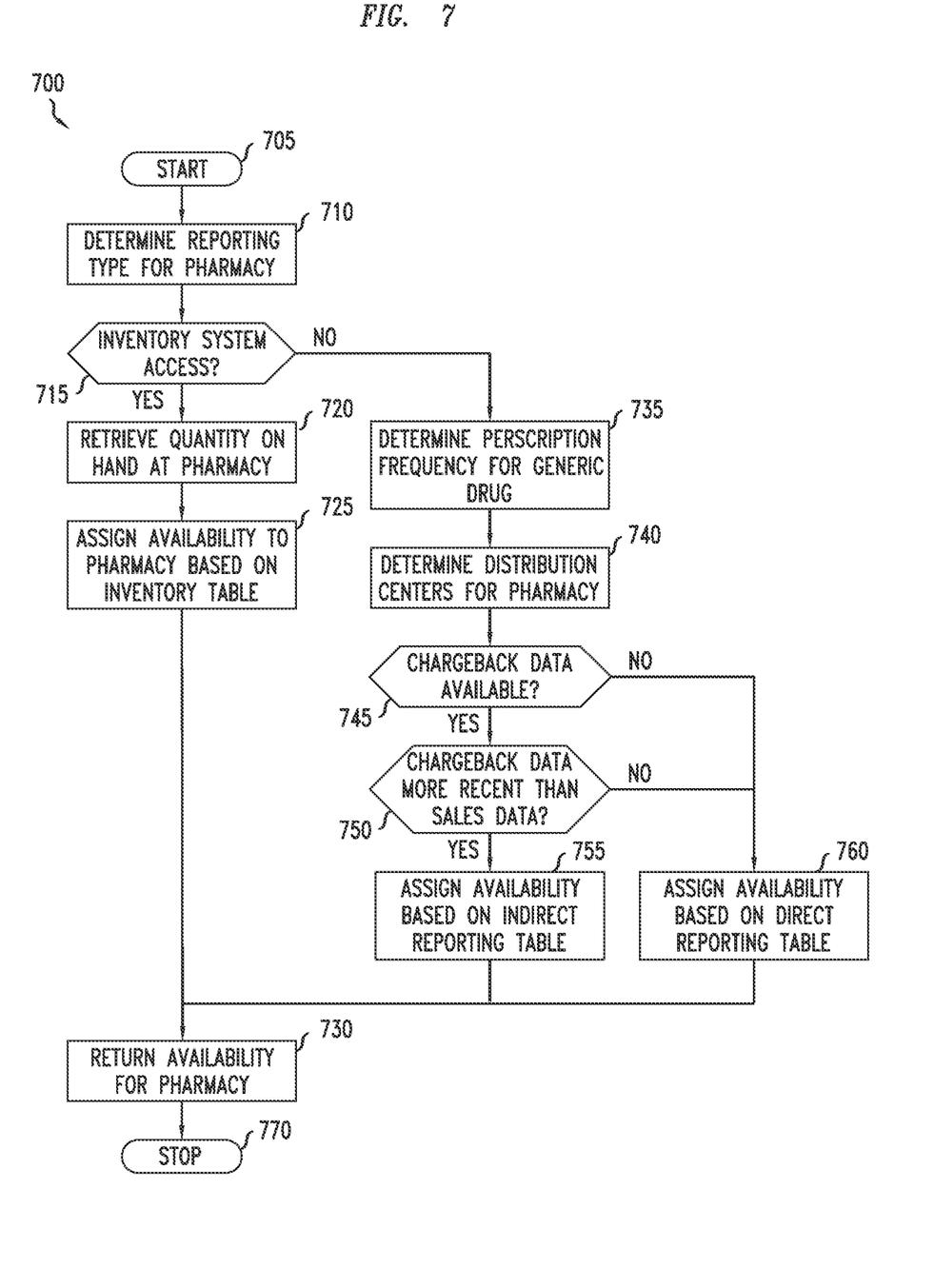
FIG. 7 illustrates an exemplary method for estimating generic pharmaceutical availability.

FIG. 7 illustrates an exemplary method 700 for estimating generic pharmaceutical availability. The method 700 may be performed by the components of an application server such as, for example the application server 130 of FIG. 1 or the components of the hardware device 200 of FIG. 2. In various embodiments, the method 700 is performed in response to another method or process invoking a rules engine, such as in step 625 of method 600.

The method begins in step 705 and proceeds to step 710 where the application server determines a reporting type for the pharmacy. For example, based on pharmacy records, the application server may determine whether the pharmacy provides direct inventory access or whether only distribution center transaction data is available for the pharmacy. In step 715, the method 700 determines whether the reporting type was identified as direct inventory access in step 715. If so, the method 700 proceeds to step 720 where the application server retrieves the quantity on hand at the pharmacy directly. For example, the application server may transmit a query to the pharmacy's inventory system or may read from a database of previously-retrieved inventory data. In step 725, the application server applies a table associated with inventory system access to the retrieved quantity to determine an availability. An example of such an "inventory table" will be described below. The application server then returns the determined availability to the requesting method in step 730.

If, on the other hand, the pharmacy does not provide direct inventory system access, the method 700 proceeds instead from step 715 to step 735 where the application server will determine a prescription frequency associated with the generic drug. For example, the application server may refer to a lookup table to determine whether the drug is associated with a "slow," "medium," or "fast" prescription frequency. Then, in step 740, the application server determines one or more distribution centers that are known to distribute pharmaceuticals to the pharmacy. Again, the application server may refer to a lookup table or another record associated with the pharmacy that holds such information.

In step 745, the application server determines whether chargeback data is available from the distribution centers. As will be understood, chargeback data may indicate when and in what quantities pharmaceuticals have been distributed to pharmacies on an individual pharmacy basis. If chargeback data is available, the application server determines whether the chargeback data is more recent than the most recent sales data for the distribution centers. As will be understood, sales data may indicated when and in what quantities pharmaceuticals have been provided by the pharmaceutical manufacturer to the distribution centers. If so, the method 700 proceeds to step 755 where the application server uses the chargeback data in conjunction with an "indirect reporting table" (an example of which will be described in greater detail below) to assign an availability to the pharmacy.

If, on the other hand, chargeback data is unavailable or if sales data that is more recent than the available chargeback data is available, the method 700 proceeds to step 760 instead of step 755. In step 760, the application server uses the available sales data in conjunction with a "direct reporting table" (an example of which will be described in greater detail below) to assign an availability to the pharmacy. In any case, after the application server returns the determined availability to the invoking process in step 730 and the method 700 proceeds to end in step 770.

Figure 8:
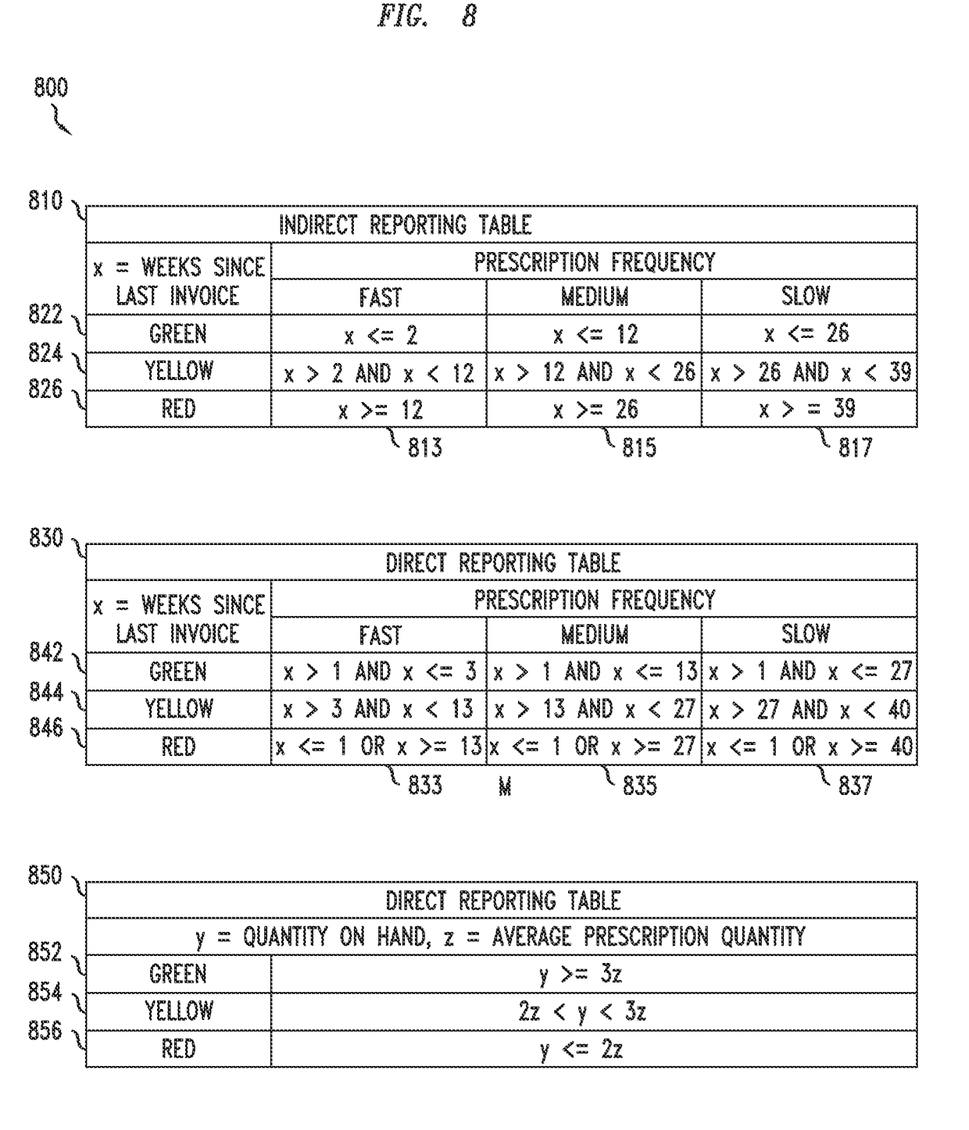
FIG. 8 illustrates an exemplary rule set for estimating generic pharmaceutical availability.

FIG. 8 illustrates an exemplary rule set 800 for estimating generic pharmaceutical availability. The rules set 800 may include three different rule tables 810, 830, 850 for determining pharmaceutical availabilities based on different available information. Various modifications to the rule set 800 will be apparent. For example, different rule sets may be defined for different pharmaceuticals, additional rule tables may be defined to take into account different types of data from which generic drug availability at a pharmacy may be inferred, or fewer or additional availability levels may be defined and in different manners than color codes. Additionally or alternatively, more complex rule sets may be defined to take into account additional information such as the quantity of a generic pharmaceutical provided in connection with a sale or chargeback.

A first table is shown to be an "indirect reporting table" 810 for use in determining generic drug availability based on chargeback information. The indirect reporting table 810 determines an availability of a pharmaceutical based on two pieces of information: a prescription frequency for the drug in question and the number of weeks since the last chargeback was entered or otherwise occurred. To take into account the prescription frequency, three columns are provided in the table: a "fast column" 813, a "medium column" 815, and a "slow column" 817. After selecting the corresponding column for the drug, the rules engine may select the corresponding row 822, 824, 826 based on the number of weeks since the last chargeback to determine an availability level "green" "yellow" or "red." For example, for a generic drug that is deemed to be prescribed with a "slow" frequency where the most recent chargeback occurred 30 weeks ago, the application server may select column 817 as applicable and, subsequently, select row 824 as applicable, thereby determining that a "yellow" availability should be returned.

A second table is shown as a "direct reporting table" 830 for use in determining generic drug availability based on sales transaction data. The direct reporting table 830 determines an availability of a pharmaceutical based on two pieces of information: a prescription frequency for the drug in question and the number of weeks since the last sale was entered or otherwise occurred. To take into account the prescription frequency, three columns are provided in the table: a "fast column" 833, a "medium column" 835, and a "slow column" 837. After selecting the corresponding column for the drug, the rules engine may select the corresponding row 842, 844, 846 based on the number of weeks since the last sale to determine an availability level "green" "yellow" or "red." For example, for a generic drug that is deemed to be prescribed with a "medium" frequency where the most recent sale occurred 3 weeks ago, the application server may select column 835 as applicable and, subsequently, select row 842 as applicable, thereby determining that a "green" availability should be returned. As another example, for a generic drug that is deemed to be prescribed with a "medium" frequency where the most recent sale occurred less than a week ago, the application server may select column 835 as applicable and, subsequently, select row 846 as applicable, thereby determining that a "red" availability should be returned (because, within a week, an application server may assume in some embodiments that the pharmaceutical has not had time to be received and redistributed to the pharmacy by the distribution center).

A third table is shown to be an "inventory table" 850 for use in determining generic drug availability based on directly accessing a pharmacy's inventory system. The inventory table 850 determines an availability of a pharmaceutical based on two pieces of information: an amount of the drug currently on hand at the pharmacy and the amount of the drug that is prescribed on average (which may be obtained, for example, via a lookup table). Based on this information, the rules engine is able to select an applicable row 852, 854, 856 to determine the availability to return. For example, where the pharmacy has 180 units of a generic drug on hand and that drug is usually prescribed 30 units at a time, the rules engine may select row 852 as applicable (180>3*30) and, accordingly, return a "green" level of availability.

It will be appreciated that, while various example embodiments are described herein, various modifications to these examples may be made. For example, various alternative embodiments may enable to user to input multiple drug names. In such embodiments, the application server may attempt to return a list of pharmacies that stock the Mylan version of each such drug. In other embodiments, other data may be used to determine availability of a drug at a particular pharmacy. For example, a barcode or other tracking system may be implemented to provide real-time data of the location of generic pharmaceuticals or containers thereof. In other embodiments, an RFID chip or other smart tag may be affixed to drug containers; thereafter, such chips or tags may communicate via a network with the application server to inform the server of the location of each container. Various modifications for utilizing such real-time data to determine pharmaceutical availability will be apparent.

According to the foregoing, various exemplary embodiments provide for systems and methods for providing patients the ability to determine which local pharmacies carry a generic version of prescribed drug as manufactured by a particular and preferred pharmaceutical manufacturer such as Mylan, Inc. Further, various embodiments enable the determination of pharmaceutical availability on a per pharmacy basis given varying degrees of information regarding the pharmaceuticals actually on hand. Various additional benefits will be apparent in view of the foregoing.

It should be apparent from the foregoing description that various exemplary embodiments of the invention may be implemented in hardware and/or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principals of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A non-transitory machine-readable storage medium encoded with instructions for execution by an application server, the non-transitory machine-readable storage medium comprising:

instructions for receiving, from a user device, a request for pharmaceutical availability, the request including a pharmaceutical identification and a location of the user device;

instructions for identifying a pharmacy near the received location of the user device that is known to stock a specific non-branded pharmaceutical identified by the pharmaceutical identification that is manufactured by a specified pharmaceutical manufacturer; and instructions for transmitting the identified pharmacy to the user device, whereby the user device receives a list of at least one nearby pharmacy that carries the specific non-branded pharmaceutical manufactured by the specified pharmaceutical manufacturer;

instructions for displaying a display area on the user device including a map-style view, an information window including an availability indication, wherein the availability indication is configured to display different colors depending on an inventory condition of the specific nonbranded pharmaceutical at the identified pharmacy, and the availability indication when displaying one of the different colors is selectable by the user to initiate a phone call to the identified pharmacy;

instructions for querying the identified pharmacy to retrieve a first number for quantity on hand and a second number for average prescription quantity from the identified pharmacy; and instruction for generating a table based on inputting the first number and the second number for the availability indication, the table comprising an inventory table based on directly accessing a pharmacy's inventory system, the inventory table comprising a result when $y>=Rz$, a second result when $Mz<y<Rz$, a third result when $y<=Mz$, wherein y is the first number, z is the second number, and M and R are both positive numbers such that R is greater than M, instruction for querying the identified pharmacy to retrieve a third number for a prescription frequency for the specific non-branded pharmaceutical and a fourth number for time interval since a last sale was entered; and instruction for generating a second table based on inputting the third number and the fourth number, wherein the second table comprises a first result when $x<=F1$, a second result when $x>F1$ and $x<F2$, a third result when $x>F2$, a fourth result when $x<=F2$, a fifth result when $x>F2$ and $x<F3$, a sixth result when $x>=F3$, a seventh result when $x<=F3$, an eighth result when $x>F3$ and $x<F4$, a ninth result when $x>=F4$, wherein x is the fourth number and F1, F2, F3 and F4 are positive numbers such that $F4>F3>F2>F1$, wherein the instructions for identifying the pharmacy include server instructions for identifying pharmacies that are proximate to the user device by a spatial engine such that the user device displays a first color representing the first result when the specific non-brand pharmaceutical is available to the user, a second color representing the second result, and a third color representing the third result.

2. The non-transitory machine-readable storage medium of claim 1, further comprising:

instructions for determining an availability of the specific non-branded pharmaceutical at the identified pharmacy, wherein the instructions for transmitting the identified pharmacy to the user device comprise instructions for transmitting the identified pharmacy together with the determined availability.

3. The non-transitory machine-readable storage medium of claim 2, wherein the instructions for determining an availability of the specific non-branded pharmaceutical at the identified pharmacy comprise:

instructions for determining a frequency of prescription for the identified pharmaceutical;

instructions for determining, based on transaction data and the prescription frequency, a level of availability for the specific non-branded pharmaceutical at the identified pharmacy.

4. The non-transitory machine-readable storage medium of claim 3, wherein the instructions for determining, based on transaction data and the prescription frequency, a level of availability for the specific non-branded pharmaceutical at the identified pharmacy comprise:
   instructions for identifying an applicable rule from the rule table, wherein the applicable rule applies to the transaction data and the prescription frequency and the applicable rule indicates the level of availability.

5. The non-transitory machine-readable storage medium of claim 4, wherein the applicable rule specifies a time interval from a current date, and the transaction data includes a transaction falling within the specified time interval.

6. The non-transitory machine-readable storage medium of claim 1, wherein R is 3 and M is 2.

7. The non-transitory machine-readable storage medium of claim 1, further comprising instruction for querying the identified pharmacy to retrieve a third number for a prescription frequency for the specific non-branded pharmaceutical and a fourth number for time interval since a last chargeback was entered; and instruction for generating a second table based on inputting the third number and the fourth number, wherein the second table comprises a first result when x>F1 and x<=F2, a second result when x>F2 and x<F3, a third result when x<=F1 or x>=F3, a fourth result when x>F1 and x<=F3, a fifth result when x>F3 and x<F4, a sixth result when x<=F1 or x>=F4, a seventh result when x>1 and x<=F4, an eighth result when x>F4 and x<F5, a ninth result when x<=F1 or x>=F5, wherein x is the fourth number and F1, F2, F3 and F4 are positive numbers such that F4>F3>F2>F1.

8. An application server comprising:
   a memory;
   a network interface; and a processor in communication with the memory and the network interface, wherein the processor is configured to:
   receive, via the network interface from a user device, a request for pharmaceutical availability, the request including a pharmaceutical identification and a location of the user device,
   identify a pharmacy near the received location of the user device that is known to stock a specific non-branded pharmaceutical identified by the pharmaceutical identification that is manufactured by a specified pharmaceutical manufacturer, and
   transmit the identified pharmacy to the user device via the network interface, whereby the user device receives a list of at least one nearby pharmacy that carries the specific non-branded pharmaceutical manufactured by the specified pharmaceutical manufacturer;
   display a display area on the user device including a map-style view, an information window including an availability indication, wherein the availability indication is configured to display different colors depending on an inventory condition of the specific nonbranded pharmaceutical at the identified pharmacy, and the availability indication when displaying one of the different colors is selectable by the user to initiate a phone call to the identified pharmacy;
   query the identified pharmacy to retrieve a first number for quantity on hand and a second number for average prescription quantity from the identified pharmacy; and
   generate a table based on the first number and the second number for the availability indication, and the table comprising an inventory table based on directly accessing a pharmacy's inventory system, the table comprising an inventory table based on directly accessing a pharmacy's inventory system, the inventory table comprising a first result when y>=Rz, a second result when Mz<y<Rz, a third result when y<=Mz,
   wherein y is the first number, z is the second number, and M and R are both positive numbers such that R is greater than M, wherein R is 3 and M is 2,
   wherein identifying the pharmacy includes accessing the table for different pharmaceuticals, pharmacy data, availability levels, and quantity of the specific non-branded pharmaceutical in connection with a sale or charge back such that the user device displays a first color representing the first result when the specific non-brand pharmaceutical is available to the user, a second color representing the second result, and a third color representing the third result.

9. The application server of claim 8, wherein the processor is further configured to:
   determine an availability of the specific non-branded pharmaceutical at the identified pharmacy,
   wherein in transmitting the identified pharmacy to the user device, the processor 1 s configured to transmit the identified pharmacy together with the determined availability.

10. The application server of claim 9, wherein in determining an availability of the specific non-branded pharmaceutical at the identified pharmacy the processor is configured to:
    determine a frequency of prescription for the identified pharmaceutical;
    determine, based on transaction data and the prescription frequency, a level of availability for the specific non-branded pharmaceutical at the identified pharmacy.

11. The application server of claim 10, wherein the transaction data is sales data describing at least one sales transaction providing the specific non-branded pharmaceutical to a distribution center associated with the pharmacy.

12. The application server of claim 10, wherein the transaction data is chargeback data describing at least one distribution transaction providing the specific non-branded pharmaceutical to the pharmacy from a distribution center associated with the pharmacy.

13. The application server of claim 10, wherein in determining, based on transaction data and the prescription frequency, a level of availability for the specific non-branded pharmaceutical at the identified pharmacy the processor is configured to:
    identify an applicable rule from the rule table, wherein the applicable rule applies to the transaction data and the prescription frequency and the applicable rule indicates the level of availability.

14. A method performed by an application server, the method comprising:
    receiving, from a user device, a request for pharmaceutical availability, the request including a pharmaceutical identification and a location of the user device;
    identifying a pharmacy near the received location of the user device that is known to stock a specific non-branded pharmaceutical identified by the pharmaceutical identification that is manufactured by a specified pharmaceutical manufacturer;
    transmitting the identified pharmacy to the user device, whereby the user device receives a list of at least one nearby pharmacy that carries the specific non-branded pharmaceutical manufactured by the specified pharmaceutical manufacturer;

displaying a display area on the user device including a map-style view, an information window including an availability indication, wherein the availability indication is configured to display different colors depending on an inventory condition of the specific nonbranded pharmaceutical at the identified pharmacy, and the availability indication when displaying one of the different colors is selectable by the user to initiate a phone call to the identified pharmacy;

querying the identified pharmacy to retrieve a first number for quantity on hand and a second number for average prescription quantity from the identified pharmacy; and generating a table based on inputting the first number and the second number for the availability indication, the table comprising an inventory table based on directly accessing a pharmacy's inventory system, the inventory table comprising a first result when $y \geq Rz$, a second result when $Mz < y < Rz$, a third result when $y \leq Mz$, wherein y is the first number, z is the second number, and M and R are both positive numbers such that R is greater than M, wherein R is 3 and M is 2, wherein identifying the pharmacy includes determining the availability of the specific nonbranded pharmaceuticals from the specified manufacturer at each pharmacy by a rules engine such that the user device displays a first color representing the first result when the specific non-brand pharmaceutical is available to the user, a second color representing the second result, and a third color representing the third result.

15. The method of claim 14, further comprising: determining an availability of the specific non-branded pharmaceutical at the identified pharmacy, wherein transmitting the identified pharmacy to the user device comprises transmitting the identified pharmacy together with the determined availability.

16. The method of claim 15, wherein determining an availability of the pharmaceutical at the identified pharmacy comprises:

determining a frequency of prescription for the identified pharmaceutical;

determining, based on transaction data and the prescription frequency, a level of availability for the specific non-branded pharmaceutical at the identified pharmacy.

17. The method of claim 16, wherein the transaction data is sales data describing at least one sales transaction providing the specific non-branded pharmaceutical to a distribution center associated with the pharmacy.

18. The method of claim 16, wherein the transaction data is chargeback data describing at least one distribution transaction providing the specific non-branded pharmaceutical to the pharmacy from a distribution center associated with the pharmacy.

19. The method of claim 16, wherein determining, based on transaction data and the prescription frequency, a level of availability for the specific non-branded pharmaceutical at the identified pharmacy comprises:

identifying an applicable rule from the rule table, wherein the applicable rule applies to the transaction data and the prescription frequency and the applicable rule indicates the level of availability.

* * * * *